United States Patent
John et al.

(10) Patent No.: US 9,339,543 B2
(45) Date of Patent: May 17, 2016

(54) PHARMACEUTICAL COMPOSITIONS THAT INHIBIT DISPROPORTIONATION

(71) Applicants: Christopher T. John, Audobon, PA (US); Paul A. Harmon, Perkiomenville, PA (US)

(72) Inventors: Christopher T. John, Audobon, PA (US); Paul A. Harmon, Perkiomenville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 75 days.

(21) Appl. No.: 14/350,839

(22) PCT Filed: Oct. 8, 2012

(86) PCT No.: PCT/US2012/059172
§ 371 (c)(1),
(2) Date: Apr. 10, 2014

(87) PCT Pub. No.: WO2013/055609
PCT Pub. Date: Apr. 18, 2013

(65) Prior Publication Data
US 2014/0256772 A1    Sep. 11, 2014

Related U.S. Application Data

(60) Provisional application No. 61/546,135, filed on Oct. 12, 2011.

(51) Int. Cl.
*A61K 31/44* (2006.01)
*A01N 43/40* (2006.01)
*A61K 47/12* (2006.01)
*A61K 9/20* (2006.01)
*A61K 31/4439* (2006.01)

(52) U.S. Cl.
CPC .............. *A61K 47/12* (2013.01); *A61K 9/2013* (2013.01); *A61K 31/4439* (2013.01); *A61K 9/2054* (2013.01)

(58) Field of Classification Search
CPC . A61K 31/4439; A61K 47/12; A61K 9/2013; A61K 9/2054
USPC .......................................................... 514/342
See application file for complete search history.

(56) References Cited

U.S. PATENT DOCUMENTS

| 2004/0097424 A1 | 5/2004 | Glombik et al. |
| 2006/0280794 A1 | 12/2006 | Hamaguchi et al. |
| 2010/0166853 A1 | 7/2010 | Bando et al. |
| 2011/0039763 A1 | 2/2011 | Eckert et al. |

FOREIGN PATENT DOCUMENTS

| WO | WO9826765 A1 | 6/1998 |
| WO | WO9955320 A1 | 11/1999 |
| WO | WO2010/120963 A1 | 10/2010 |
| WO | WO2011/138380 A1 | 11/2011 |

OTHER PUBLICATIONS

Enalapril maleate salt, Product Information from Sigma Jan. 2004, https://www.sigmaaldrich.com/content/dam/sigma-aldrich/docs/Sigma/Product_Information_Sheet/e6888pis.pdf.*
Stephenson, et al.: Physical stability of salts of weak bases in the solid-state:, J. Pharm Sci, vol. 100(5), 2010, pp. 1607-1617.
Guerrieri, et al.: "Role of Salt and Excipient Properties on Disproportionation in the Solid-State", Pharm Res, vol. 26 (8), 2009, pp. 2015-2026.
PCT International Search Report dated Dec. 18, 2012 for related International Application No. PCT/US2012/59172; 2 pages.
Written Opinion of the PCT International Search Report dated Dec. 18, 2012 for related International Application No. PCT/US2012/59172; 2 pages.

* cited by examiner

*Primary Examiner* — My-Chau T Tran
(74) *Attorney, Agent, or Firm* — Janet E. Fair; Anna L. Cocuzzo

(57) ABSTRACT

Pharmaceutical formulations comprising solid pharmaceutically acceptable organic acids, such as maleic acid or tartaric acid, that inhibit the disproportionation of pharmaceutically acceptable acid salts of active pharmaceutical ingredients, and methods of manufacturing such pharmaceutical compositions. The pharmaceutically acceptable acid salt of the active pharmaceutical ingredient has a pKa of less than about 6.0, and wherein the solid pharmaceutically acceptable organic acid has a pKa of less than about 4.0 and an aqueous solubility in the range of about 500 to about 2000 milligrams per milliliter. A pharmaceutical formulation comprising a pharmaceutical acceptable acid salt of pioglitazone, a solid pharmaceutically acceptable organic acid selected from the group consisting of maleic acid or tartaric acid, and an excipient that promotes disproportionation, wherein the ratio by weight of the solid pharmaceutically acceptable organic acid to excipient is from about 1:6 to about 1:1.

12 Claims, 7 Drawing Sheets

US 9,339,543 B2

PHARMACEUTICAL COMPOSITIONS THAT INHIBIT DISPROPORTIONATION

FIELD OF THE INVENTION

The subject invention is directed to pharmaceutical formulations containing solid pharmaceutically acceptable organic acids, such as maleic acid or tartaric acid, that inhibit the disproportionation of pharmaceutically acceptable acid salts of active pharmaceutical ingredients.

BACKGROUND OF THE INVENTION

Numerous therapeutic agents exist as crystalline salts, in which a relatively basic site on the drug molecule is protonated and accompanied by a nearby counterion of negative charge. Such salts typically have significant advantages in solubility and bioavailability over the neutral crystalline API forms. However, if the pKa of the API basic site is too low, there is a risk that over long term storage of the tablets, disproportionation, or proton transfer, can occur when the API salt is formulated with standard oral tablet dosage form excipients with basic sites such as magnesium stearate and croscarmellose sodium. Such disproportionation leads to formation of the neutral free base form of the drug which can significantly reduce the bioavailability of the drug and thus dramatically impact the quality of the formulated drug product.

This invention describes the inclusion of pharmaceutically acceptable organic acid compounds, such as maleic and tartaric acids, into pharmaceutical formulations of API salts with relatively low pKa's that are prone to disproportionation. Inclusion of acid compounds, such as maleic and tartaric acids, at relatively low weight percentage in tablets is expected to significantly reduce overall amount of form conversion caused by proton transfer mediated disproportionation. In addition, the inclusion of acid compounds, such as maleic and tartaric acids, are expected to allow for the use of certain excipients known to promote disproportionation such as magnesium stearate, sodium stearyl fumarate, and/or croscarmellose sodium which have critical functionalities in many tablet formulations. Thus, the invention will allow for more robust and effective oral tablet formulations of low pKa API salts.

SUMMARY OF THE INVENTION

The invention is directed to a pharmaceutical formulation comprising a pharmaceutically acceptable acid salt of an active pharmaceutical ingredient, and a solid pharmaceutically acceptable organic acid in a sufficient amount to reduce disproportionation, wherein the pharmaceutically acceptable acid salt of the active pharmaceutical ingredient has a pKa of less than about 6.0, and wherein the solid pharmaceutically acceptable organic acid has a pKa of less than about 4.0 and an aqueous solubility in the range of about 500 to about 2000 milligrams per milliliter.

The invention is also directed to a method of manufacturing a pharmaceutical formulation comprising an active pharmaceutical ingredient and an excipient promoting disproportionation, comprising the step of adding a pharmaceutically acceptable organic acid in a sufficient amount to reduce disproportionation, wherein the solid pharmaceutically acceptable organic acid has a pKa of less than about 4.0 and an aqueous solubility in the range of about 500 to about 2000 milligrams per milliliter.

The invention is also directed to a pharmaceutical formulation comprising a pharmaceutical acceptable acid salt of pioglitazone, a solid pharmaceutically acceptable organic acid selected from the group consisting of maleic acid or tartaric acid, and an excipient that promotes disproportionation, wherein the ratio by weight of the solid pharmaceutically acceptable organic acid to excipient is from about 1:6 to about 1:1.

DETAILED DESCRIPTION OF THE INVENTION

Figure 1:
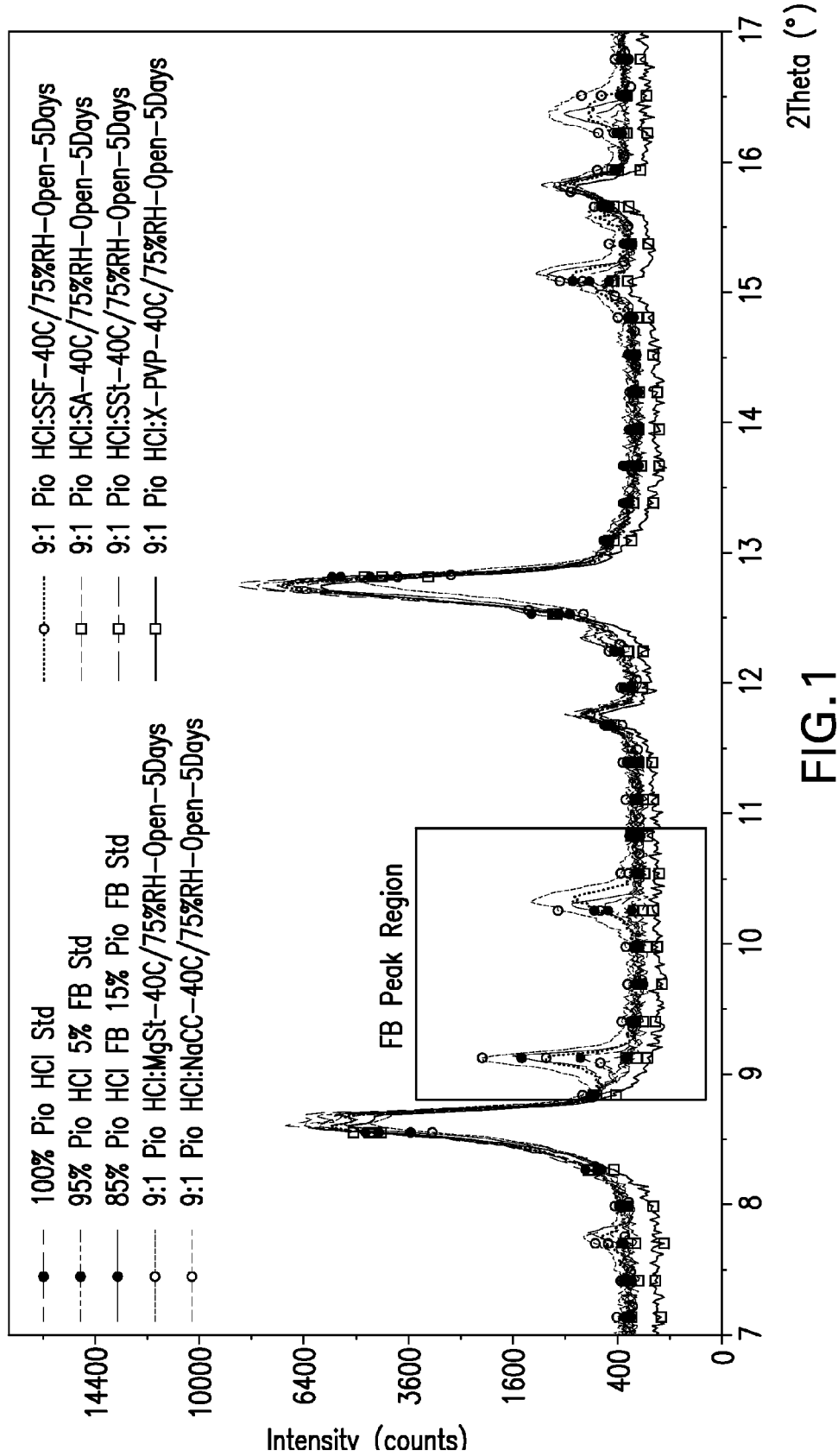
FIG. 1 shows X-ray powder diffraction of compacts of pioglitazone HCl, pioglitazone free base standards, and binary compacts of pioglitazone HCl with various excipients.

In one embodiment, the invention is directed to a pharmaceutical formulation, wherein the pharmaceutically acceptable acid salt of the active pharmaceutical ingredient has a pKa of less than about 6.0. In one class of this embodiment, the pharmaceutically acceptable acid salt of the active pharmaceutical ingredient has a pKa of less than about 5.6. In one class of this embodiment, the pharmaceutically acceptable acid salt of the active pharmaceutical ingredient has a pKa of less than about 5.0. In one class of this embodiment, the pharmaceutically acceptable acid salt of the active pharmaceutical ingredient has a pKa of less than about 4.0. In one class of this embodiment, the pharmaceutically acceptable acid salt of the active pharmaceutical ingredient has a pKa of less than about 3.0. In one class of this embodiment, the pharmaceutically acceptable acid salt of the active pharmaceutical ingredient has a pKa of about 5.6.

In one embodiment, the invention is directed to a pharmaceutical formulation, wherein the solid pharmaceutically acceptable organic acid has a pKa range of less than about 4.0. In one class of this embodiment, the solid pharmaceutically acceptable organic acid has a pKa range of about 1.0 to about 4.0. In one class of this embodiment, the solid pharmaceutically acceptable organic acid has a pKa range of about 1.5 to about 3.5. In one class of this embodiment, the solid pharmaceutically acceptable organic acid has a pKa range of about 1.5 to about 2.5. In one class of this embodiment, the solid pharmaceutically acceptable organic acid has a pKa range of about 3.0 to about 4.0. In one class of this embodiment, the solid pharmaceutically acceptable organic acid has a pKa range of about 2.5 to about 3.5. In one class of this embodiment, the solid pharmaceutically acceptable organic acid has a pKa of about 1.9. In one class of this embodiment, the solid pharmaceutically acceptable organic acid has a pKa of about 2.95. In one class of this embodiment, the solid pharmaceutically acceptable organic acid has a pKa of about 3.2.

In one embodiment, the invention is directed to a pharmaceutical formulation, wherein the solid pharmaceutically acceptable organic acid has a solubility range of about 500 to about 2000 milligrams per milliliter. In one class of this embodiment, the solid pharmaceutically acceptable organic acid has a solubility range of about 500 to about 1500 milligrams per milliliter. In one class of this embodiment, the solid pharmaceutically acceptable organic acid has a solubility range of about 700 to about 1500 milligrams per milliliter. In one class of this embodiment, the solid pharmaceutically acceptable organic acid has a solubility range of about 700 to about 800 milligrams per milliliter. In another embodiment, the solid pharmaceutically acceptable organic acid has a solubility range of about 1000 to about 1500 milligrams per milliliter.

In one embodiment, the invention is directed to a pharmaceutical formulation, wherein the pharmaceutically acceptable organic acid has a pKa of less than about 4.0 and an aqueous solubility in the range of about 500 to about 2000 milligrams per milliliter. In one class of this embodiment, the pharmaceutically acceptable organic acid has a pKa in the range of about 1.0 to about 4.0 and an aqueous solubility in the range of about 500 to about 1500 milligrams per milliliter. In one class of this embodiment, the pharmaceutically acceptable organic acid has a pKa in the range of about 1.0 to about 2.0 and an aqueous solubility in the range of about 500 to about 1000 milligrams per milliliter. In one class of this embodiment, the solid pharmaceutically acceptable organic acid has a pKa in the range of about 2.5 to about 3.5 and an aqueous solubility in the range of about 1000 to about 1500 milligrams per milliliter. In one class of this embodiment, the solid pharmaceutically acceptable organic acid has a pKa in the range of about 1.9, and an aqueous solubility of about 780 milligrams per milliliter. In one class of this embodiment, the solid pharmaceutically acceptable organic acid has a pKa in the range of about 2.95, and an aqueous solubility in the range of about 1330 milligrams per milliliter.

In one embodiment, the invention is directed to a pharmaceutical formulation, wherein the solid pharmaceutically acceptable organic acid is maleic acid or tartaric acid. In another embodiment, the solid pharmaceutically acceptable organic acid is maleic acid. In another embodiment, the solid pharmaceutically acceptable organic acid is tartaric acid.

In one embodiment, the invention is directed to a pharmaceutical formulation, wherein the pharmaceutical formulation further comprises excipients that promote disproportionation. Typically, excipients that promote disproportionation are compounds containing carboxylate salt functional groups. Non-limiting examples of excipients that promote disproportionation include magnesium stearate, sodium stearyl fumarate, or croscarmellose sodium, or combinations thereof.

In one class of this embodiment, the excipient that promotes disproportionation is magnesium stearate. In one class of this embodiment, the excipient that promotes disproportionation is sodium stearyl fumarate. In another embodiment, the excipient that promotes disproportionation is croscarmellose sodium.

In one embodiment, the invention is directed to a pharmaceutical formulation, wherein the ratio by weight of the solid pharmaceutically acceptable organic acid to excipient that promotes disproportionation is from about 1:6 to about 1:1, respectively. In one class of this embodiment, the ratio by weight of the solid pharmaceutically acceptable organic acid to excipient that promotes disproportionation is from about 1:2 to about 1:1, respectively. In one class of this embodiment, the ratio by weight of the solid pharmaceutically acceptable organic acid to excipient that promotes disproportionation is about 1:1.

In one embodiment, the invention is also directed to a method of manufacturing a pharmaceutically acceptable acid salt of an active pharmaceutical ingredient, wherein the pKa is less than 6.0, in a pharmaceutical formulation, comprising adding to the formulation a pharmaceutically acceptable organic acid, wherein the solid pharmaceutically acceptable organic acid has a pKa of less than about 4.0 and an aqueous solubility in the range of about 500 to about 2000 milligrams per milliliter.

In one class of this embodiment, the pharmaceutically acceptable organic acid is added in a sufficient amount such that the ratio of the pharmaceutically acceptable organic acid to excipient that promotes disproportionation is from about 1:6 to about 1:1. In another class of this embodiment, the pharmaceutically acceptable organic acid is added in a sufficient amount such that the ratio of the pharmaceutically acceptable organic acid to excipient that promotes disproportionation is from about 1:2 to about 1:1. In another class of this embodiment, the pharmaceutically acceptable organic acid is added in a sufficient amount such that the ratio of the pharmaceutically acceptable organic acid to excipient that promotes disproportionation is about 1:1.

Active Pharmaceutical Ingredients (API)

The API's of the present invention include the pharmaceutically acceptable acid salt of the API's. Generally, the lower the pKa of such API's (less than about 6.0), the more readily disproportionation occurs. Non-limiting examples of such API's include the pharmaceutically acceptable acid salts of analgesic agents, anesthetic agents, anti-anginal agents, anti-arthritic agents, anti-arrhythmic agents, anti-asthmatic agents, anti-bacterial agents, anti-benign prostatic hyperplasia agents, anti-cancer agents, anti-cholinergic agents, anti-coagulants, anti-convulsants, anti-depressants, anti-diabetic agents, anti-diarrheals, anti-epileptic agents, anti-fungal agents, anti-gout agents, anti-helminthic agents, anti-histamines, anti-hypertensive agents, anti-inflammatory agents, anti-malarial agents, anti-migraine agents, anti-muscarinic agents, anti-nauseants, anti-neoplastic agents, anti-obesity agents, anti-osteoporosis agents, anti-parkinsonism agents, anti-protozoal agents, anti-pruritics, anti-psychotic agents, anti-pyretics, anti-spasmodics, anti-thyroid agents, anti-tubercular agents, anti-ulcer agents, anti-urinary incontinence agents, anti-viral agents, anxiolytic agents, appetite suppressants, attention deficit disorder and attention deficit hyperactivity disorder drugs, calcium channel blockers, cardiac inotropic agents, beta-blockers, central nervous system stimulants, cognition enhancers, corticosteroids, COX-2 inhibitors, decongestants, diuretics, gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, parasympatholytic agents, sedatives, sex hormones, sympathomimetic agents, tranquilizers, vasodilators, vitamins, and mixtures thereof.

An API relevant to this invention is pioglitazone hydrochloride. Pioglitazone hydrochloride is a thiazolidinedione PPAR-γ agonist used in the management of type 2 diabetes mellitus (also known as non-insulin dependent diabetes mellitus or adult onset diabetes) primarily by decreasing insulin resistance. Pharmacological studies indicate that pioglitazone hydrochloride improves sensitivity to insulin in muscle and adipose tissue, inhibits hepatic gluconeogenesis, and improves glycemic control while reducing circulating insulin levels.

Pioglitazone hydrochloride once formulated has been found to react with excipients such as magnesium stearate and sodium stearyl fumarate, resulting in disproportionation of the pioglitazone hydrochloride to the pioglitazone free base.

In one embodiment, the invention is directed to a pharmaceutical formulation comprising:
(1) a pharmaceutically acceptable acid salt of pioglitazone,
(2) a solid pharmaceutically acceptable organic acid selected from the group consisting of maleic acid or tartaric acid, and
(3) an excipient that promotes disproportionation,
wherein the ratio by weight of the solid pharmaceutically acceptable organic acid to excipient is from about 1:6 to about 1:1.

In one embodiment, the ratio by weight of the solid pharmaceutically acceptable organic acid to excipient is from about 1:2 to about 1:1. In one class of this embodiment, the ratio by weight of the solid pharmaceutically acceptable organic acid to excipient is about 1:1.

In one embodiment, the excipient that promotes disproportionation is selected from the group consisting of magnesium stearate, sodium stearyl fumarate, croscarmellose sodium, or combinations thereof.

In one class of this embodiment, the excipient that promotes disproportionation is magnesium stearate. In another class of this embodiment, the excipient that promotes disproportionation is sodium stearyl fumarate. In another class of this embodiment, the excipient that promotes disproportionation is croscarmellose sodium.

In one class of this embodiment, the solid pharmaceutically acceptable organic acid is maleic acid. In one subclass of this class, the excipient is magnesium stearate. In one subclass of this class, the excipient is sodium stearyl fumarate. In one subclass of this class, the excipient is croscarmellose sodium.

In one class of this embodiment, the solid pharmaceutically acceptable organic acid is tartaric acid. In one subclass of this class, the excipient is magnesium stearate. In one subclass of this class, the excipient is sodium stearyl fumarate. In one subclass of this class, the excipient is croscarmellose sodium.

Preparation of Formulations

The pharmaceutical compositions of the present invention are prepared by wet processing methods. In one embodiment the pharmaceutical compositions are prepared by wet granulation methods, such as fluid bed granulation or high-shear granulation. In a class of this embodiment, the pharmaceutical compositions are prepared by fluid-bed granulation. Fluid bed granulation processing has the advantage of affording tablets with higher diametric strength.

The pharmaceutical compositions of the present invention are prepared by a dry granulation method.

Dry granulation, wet granulation and fluid bed granulation processes are described in Remington's "The Science and Practice of Pharmacy," $21^{st}$ ed. (2006), pp. 896-901.

The pharmaceutical compositions obtained by the wet or dry processing methods may be compressed into tablets, encapsulated, or metered into sachets.

In one embodiment of the invention, the solid dosage formulations are tablets.

Excipients

The pharmaceutical compositions contain one or more lubricants or glidants. Examples of lubricants include magnesium stearate, calcium stearate, stearic acid, sodium stearyl fumarate, hydrogenated castor oil, and mixtures thereof. In one embodiment, the lubricant is magnesium stearate or sodium stearyl fumarate, or a mixture thereof. In another embodiment, the lubricant is a mixture of magnesium stearate and sodium stearyl fumarate. In another embodiment, the lubricant is magnesium stearate. In another embodiment, the lubricant is sodium stearyl fumarate. Examples of glidants include colloidal silicon dioxide, calcium phosphate tribasic, magnesium silicate, and talc.

The pharmaceutical compositions of the present invention optionally contain one or more binding agents. Embodiments of binding agents include hydroxypropylcellulose (HPC), hydroxypropylmethyl cellulose (HPMC), hydroxyethyl cellulose, starch 1500, polyvinylpyrrolidone (povidone), and co-povidone. In one embodiment, the binding agent is polyvinylpyrrolidone. In another embodiment, the binding agent is hydroxypropylcellulose (HPC). In another embodiment, the binding agent is hydroxypropylcellulose (HPC) in solution. In another embodiment, the binding agent is hydroxypropylcellulose (HPC) in an aqueous solution.

The pharmaceutical compositions of the present invention may also optionally contain one or more diluents. Examples of diluents include mannitol, sorbitol, dibasic calcium phosphate dihydrate, anhydrous dibasic calcium phosphate (also known as anhydrous dicalcium phosphate), microcrystalline cellulose, and powdered cellulose. In one embodiment, the diluent is microcrystalline cellulose. Microcrystalline cellulose is available from several suppliers and includes Avicel PH 101, Avicel PH 102, Avicel, PH 103, Avicel PH 105, and Avicel PH 200, manufactured by the FMC Corporation.

The pharmaceutical compositions of the present invention may also optionally contain a disintegrant. The disintegrant may be one of several modified starches, modified cellulose polymers, or polycarboxylic acids, such as croscarmellose sodium, sodium starch glycolate, polacrillin potassium, carboxymethylcellulose calcium (CMC Calcium), and crospovidone. In one embodiment, the disintegrant is selected from: polacrillin potassium, carboxymethylcellulose calcium (CMC Calcium), and crospovidone. In another embodiment, the disintegrant is crospovidone.

The pharmaceutical compositions of the present invention may also optionally contain one or more surfactants or wetting agents. The surfactant may be anionic, cationic, or neutral. Anionic surfactants include sodium lauryl sulfate, sodium dodecanesulfonate, sodium oleyl sulfate, and sodium laurate mixed with stearates and talc. Cationic surfactants include benzalkonium chlorides and alkyltrimethylammonium bromides. Neutral surfactants include glyceryl monooleate, polyoxyethylene sorbitan fatty acid esters, polyvinyl alcohol, and sorbitan esters. Embodiments of wetting agents include poloxamer, polyoxyethylene alkyl ethers, polyoxyethylene castor oil derivatives, and polyoxyethylene stearates.

The pharmaceutical compositions of the present invention may also optionally contain an antioxidant which may be added to the formulation to impart chemical stability. The antioxidant is selected from the group consisting of α-tocopherol, γ-tocopherol, δ-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), and butylated hydroxyanisole (BHA). In one embodiment, the antioxidant is BHT or BHA.

Preferred dosage forms for the pharmaceutical compositions of the present invention are tablets which are prepared by compression methods. Such tablets may be film-coated such as with a mixture of hydroxypropylcellulose and hydroxypropylmethylcellulose containing titanium dioxide and/or other coloring agents, such as iron oxides, dyes, and lakes; a mixture of polyvinyl alcohol (PVA) and polyethylene glycol (PEG) containing titanium dioxide and/or other coloring agents, such as iron oxides, dyes, and lakes; or any other suitable immediate-release film-coating agent(s). The coat provides taste masking and additional stability to the final tablet. A commercial film-coating agent is Opadry® which is a formulated powder blend provided by Colorcon. Embodiments of Opadry® useful in the present invention include, but are not limited to, Opadry® I (HPC/HPMC), Opadry® 20A18334, Opadry® II, Opadry® II HP (PVA-PEG), or another suitable Opadry® suspension (such as polyvinyl alcohol, polyethylene glycol, titanium dioxide, and talc, with or without colorants).

A sweetening agent and/or flavoring agent may be added if desired.

Definitions

A "therapeutically effective amount" or "effective amount" means the amount of an API, or salt or solvate thereof (e.g., the amount of API, or a salt or solvate thereof) that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "pharmaceutically acceptable," when used alone in such phrases as "pharmaceutically acceptable excipient," "pharmaceutically acceptable diluent," "pharmaceutically acceptable carrier," and "pharmaceutically acceptable adjuvant", mean an excipient, diluent, carrier, adjuvant or similar materials that are useful in preparing a pharmaceutical formulations that are generally safe, non-toxic and neither biologically nor otherwise-undesirable, and include an excipient, diluent, carrier, and adjuvant that is acceptable for veterinary use as well as human pharmaceutical use. "Pharmaceutically acceptable" materials are, within the scope of sound medical judgment, suitable for contact with the tissues of human beings and animals without excessive toxicity, irritation, allergic response, or other problem complications commensurate with a reasonable benefit/risk ratio. In some embodiments, the term "pharmaceutically acceptable" means approved by a regulatory agency of the Federal or a state government or listed in the U.S. Pharmacopoeia or other generally recognized international pharmacopoeia for use in animals, and more particularly in humans.

"A pharmaceutically acceptable excipient," or pharmaceutically acceptable "diluent," "carrier" or "adjuvant," as used in the specification and claims, includes both one and more than one such excipient, diluent, carrier, or adjuvant. An "excipients," "diluent," "carrier" or "adjuvant" refers to a substance that is used in the formulation of solid dosage pharmaceutical formulations, and, by itself, generally has little or no therapeutic value. Various excipients, diluents, carrier or adjuvants can be used in the invention, including those described in *Remington: The Science and Practice of Pharmacy*, 21$^{st}$ Ed., pp. 317-318 (2006). These include, but are not limited to, surfactants, disintegrants, fillers, antioxidants, anti-bacterial agents that prevent the decay of the formulation itself as opposed to those exhibiting a therapeutic effect, preservatives, chelating agents, buffering agents, glidants, lubricants, agents for adjusting toxicity, colorings, flavorings and diluting agents, emulsifying and suspending agents, and other substances with pharmaceutical applications.

The term "pharmaceutically acceptable acid salt," as used in the specification and claims, means a salt obtained by adding an acid to a drug molecule which protonates the drug molecule (typically on an amino group) to form a salt of the drug molecule. There may be one or more sites of protonation. Non-limiting examples of pharmaceutically acceptable acids used to make pharmaceutically acceptable acid salts are hydrochloride, hydrobromide, nitrate, sulfate, bisulfate, and citrate.

The term "solid unit dosage form," as used herein, refers to physically discrete, solid units suitable as unitary dosages for human and animal subjects, each unit containing a predetermined quantity of compounds of the present invention calculated in an amount sufficient to produce the desired effect in association with a pharmaceutically acceptable diluent, carrier or vehicle. Exemplary "solid unit dosage forms" are tablets, capsules, pills, troches, cachets and pellets. The solid dosage formulations of the invention are designed for use by an oral route of administration.

As used herein, a "pharmaceutical formulation" is meant to encompass a composition suitable for oral administration to a subject, such as a mammal, especially a human. In general a "pharmaceutical formulation" is sterile, and generally free of contaminants that are capable of eliciting an undesirable response within the subject (e.g., the compound(s) in the pharmaceutical composition is pharmaceutical grade).

Combination Therapies with the Formulation of the Invention

The above combinations include formulations of the invention not only with one other active compound, but also with two or more other active compounds. Likewise, formulations of the invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention.

In such combinations the formulation of the present invention and other active agents may be administered separately or in conjunction. In addition, the administration of one element may be prior to, concurrent to, or subsequent to the administration of other agent(s), and via the same or different routes of administration.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

"Optional" or "optionally" means that the subsequently described event, circumstance, feature, or element may, but need not, occur, and that the description includes instances where the event or circumstance occurs and instances in which it does not.

It must be noted that as used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Abbreviations

Maleic Acid: MA; Tartaric Acid: TA; Fumaric Acid: FA; Citric Acid: CA; Oxalic Acid: OA; Pioglitazone HCl: Pio-HCl; Stearic Acid: SA; Magnesium Stearate: MgSt; Sucrose Stearate: SSt; Sodium Croscarmellose NaCC; Sodium Stearyl Fumarate: SSF; Crospovidone: X-PVP; Number: No.; Weight: wt; Aqueous: Aq.; Solubility: Sol.;

EXAMPLES

The following examples are provided to more fully illustrate the invention and are not to be construed as limiting the scope of the invention, which is defined by the appended claims.

Table 1 provides a list of the organic acids along, with their pKa and aqueous solubility values, used in the studies to evaluate their potential to reduce disproportionation.

TABLE 1

Physical Properties of Selected Organic Acids

| Organic Acid | Structure | pKa Values | Aq. Sol. (g/mL) |
|---|---|---|---|
| Maleic Acid | 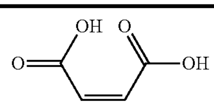 | 1.9 6.3 | 0.78 |
| Tartaric Acid | 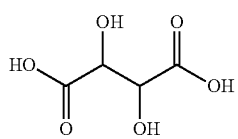 | 3.0 4.2 | 1.3 |
| Fumaric Acid | 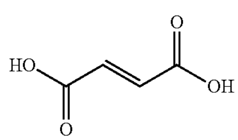 | 3.0 4.4 | $6.3 \times 10^{-3}$ |
| Citric Acid | 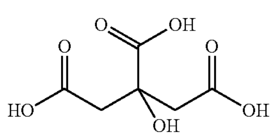 [SMILES: O=C(O)CC(O)(CC(=O)O)C(=O)O] | 3.2 4.8 6.4 | 0.6 |
| Oxalic Acid | 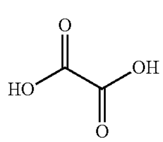 | 1.25 4.14 | 0.14 |

Exemplary Compacts of Pioglitazone HCl

An understanding of pioglitazone HCl salt disproportionation was obtained by studying each excipient individually. All of the API and excipient powders were gravimetrically dispensed into 1-dram glass vials using the Symyx Powdernium powder dispensing robot. Binary mixtures containing 250 mg of pioglitazone HCl salt and approximately 30 mg of the excipients were dispensed to create a 9:1 weight ratio mixture. Pharmaceutically relevant formulation matrix samples, or pseudo formulations, were also prepared. The compact target weight was 280 mg with a final composition of 45% of pioglitazone HCl salt, 25% avicel, 25% mannitol and 5% of the remaining excipients.

Upon completion of the powder dispensing, the vials were removed from the robot and mixed using a Resodyn Acoustic Mixer (LabRAM). The powders were mixed for 30 seconds at 30% intensity to produce homogeneous mixtures. The powders were then poured from the DRAM vial into a ½ inch die. A single compact from each DRAM vial was manually compressed using a compression force of 2000-3000 lbs and a dwell time of 5 seconds. Compacts were stressed at 40° C./35% RH and 40° C./75% RH. The sample preparation and reference for each compact can be seen in Table 2.

TABLE 2

Pioglitazone HCl Compacts

| ID # | Mass Percentage of Compacts |
|---|---|
| 1 | 100% PioHCl |
| 2 | 90% PioHCl, 10% SA |
| 3 | 90% PioHCl, 10% SSt |
| 4 | 90% PioHCl, 10% MgSt |
| 5 | 90% PioHCl, 10% NaCC |
| 6 | 90% PioHCl, 10% SSF |
| 7 | 90% PioHCl, 10% X-PVP |
| 8 | 80% PioHCl, 10% MgSt, 10% MA |
| 9 | 80% PioHCl, 10% MgSt, 10% FA |
| 10 | 80% PioHCl, 10% MgSt, 10% TA |
| 11 | 80% PioHCl, 10% MgSt, 10% CA |
| 12 | 89% PioHCl, 9.5% MgSt, 1.5% MA |
| 13 | 87% PioHCl, 10% MgSt, 3% MA |
| 14 | 85% PioHCl, 10% MgSt, 5% MA |
| 15 | 80% PioHCl, 10% MgSt, 10% OA |
| 16 | Pseudo Formulation 45% PioHCl, 50% 1:1 Avicel:Mannitol, 5% NaCC |
| 17 | Pseudo Formulation 45% PioHCl, 50% 1:1 Avicel:Mannitol, 5% SST |
| 18 | Pseudo Formulation 45% PioHCl, 50% 1:1 Avicel:Mannitol, 5% SSF |
| 19 | Pseudo Formulation 45% PioHCl, 50% 1:1 Avicel:Mannitol, 5% X-PVP |
| 20 | Pseudo Formulation 45% PioHCl, 50% 1:1 Avicel:Mannitol, 5% MgSt |
| 21 | Pseudo Formulation 45% PioHCl, 50% 1:1 Avicel:Mannitol, 5% SA |
| 22 | Pseudo Formulation 50% PioHCl, 45% 1:1 Avicel:Lactose, 5% NaCC |
| 23 | Pseudo Formulation 43% PioHCl, 47% 1:1 Avicel:Lactose, 5% NaCC, 5% MA |
| 24 | Pseudo Formulation 50% PioHCl, 45% 1:1 Avicel:Lactose, 5% SSF |
| 25 | Pseudo Formulation 43% PioHCl, 47% 1:1 Avicel:Lactose, 5% SSF, 5% MA |
| 26 | Pseudo Formulation 50% PioHCl, 45% 1:1 Avicel:Lactose, 5% MgSt |
| 27 | Pseudo Formulation 43% PioHCl, 47% 1:1 Avicel:Lactose, 5% MgSt, 5% MA |
| 28 | Pseudo Formulation 43% PioHCl, 47% 1:1 Avicel:Lactose, 5% MgSt, 5% FA |

Comparative Studies of Binary and Ternary Pioglitazone HCl Compacts Using Near-Infrared (NIR) and X-Ray Powder Diffraction (XRD) Measurements.

NIR Spectroscopy

FT-NIR reflectance spectroscopy was used to monitor the loss of HCl salt throughout the binary and pseudo formulation studies. FT-NIR spectra were obtained using a Thermo Antaris II System (Thermo Electron Co. North Carolina). All sample and standard spectra were collected with a spectral resolution of 8 $cm^{-1}$. Each spectrum is the average of 64 accumulations to produce a single spectrum with a desirable signal to noise ratio.

Calibration standards were scanned in triplicate and the spectra were chemometrically treated with a Savitsky-Golay 2nd derivative. The stressed sample compacts were scanned immediately upon removal from their respective storage chambers. Each side of the compact was scanned once per side and the two spectra were chemometrically treated with the same Savitsky-Golay $2^{nd}$ derivative.

Three factor NIR calibration models were built for Pioglitazone HCl binary and pseudo formulation samples. Both models used the spectral region from 6280-6040 cm$^{-1}$ but the pseudo formulation model also utilized a $2^{nd}$ region from 4100-4017 cm$^{-1}$.

X-Ray Powder Diffraction (XRPD) Spectroscopy

XRPD spectroscopy was also used to quantify the level of disproportionation in selected stressed samples of pioglitazone HCl. XRPD Spectroscopy is more sensitive to free base than NIR, making it suitable for samples with little or no disproportionation. The XRPD spectra were collected on the Panalytical X'pert Pro diffractometer with Cu Ka1 radition of 1.5406 Å in the transmission mode. The samples were scanned between a two theta range of 4 and 20° at a step size of 0.0167° for one hour at ambient conditions. The tube power used was 45 kV and 40 mA. In the XRPD pattern, the pioglitazone crystalline free base form has four specific peaks at $7.8_{weak}$, $9.1_{strong}$, $10.3_{strong}$ and $15.1_{moderate}$ 2-theta. The pioglitazone HCl form has a doublet peak centered at 8.6 2-theta.

The results in Tables 3 and 4 show the effect of pioglitazone HCl disproportion in various binary compacts after being stressed at 40° C./75% RH and 40° C./35% RH respectively. The NIR results indicate that HCl salt decreased to the greatest extent in compacts containing the excipient, MgSt.

TABLE 3

Pioglitazone HCl:Excipient Compacts Stressed at 40° C. and 75% Relative Humidity

| | % of Initial PioHCl Remaining | | | |
|---|---|---|---|---|
| ID No. | Day 0 | Day 0.5 | Day 3 | Day 5 |
| 100% PioHCl (1) | 100 | 101 | 100 | 98 |
| 90% PioHCl, 10% SA (2) | 100 | 99 | 100 | 99 |
| 90% PioHCl, 10% SSt (3) | 100 | 93 | 95 | 94 |
| 90% PioHCl, 10% MgSt (4) | 100 | 68 | 68 | 68 |
| 90% PioHCl, 10% NaCC (5) | 100 | 94 | 95 | 92 |
| 90% PioHCl, 10% SSF (6) | 100 | 96 | 91 | 90 |
| 90% PioHCl, 10% X-PVP (7) | 100 | 94 | 96 | 92 |

TABLE 4

Pioglitazone HCl:Excipient Compacts Stressed at 40° C. and 35% Relative Humidity

| | % of Initial PioHCl Remaining | |
|---|---|---|
| ID No. | Day 0 | Day 16 |
| 100% PioHCl (1) | 100 | 97 |
| 90% PioHCl, 10% SA (2) | 100 | 98 |
| 90% PioHCl, 10% SSt (3) | 100 | 95 |
| 90% PioHCl, 10% MgSt (4) | 100 | 72 |
| 90% PioHCl, 10% NaCC (5) | 100 | 93 |
| 90% PioHCl, 10% SSF (6) | 100 | 96 |
| 90% PioHCl, 10% X-PVP (7) | 100 | 94 |

The MR results were confirmed by analyzing select, end of the study samples stored at 40° C./75% RH with an orthogonal X-ray powder diffraction patterns (XRPD) method. FIG. 1 shows X-ray powder diffraction of various pioglitazone HCl and free base standards (solid circles), stressed 9:1 binary compacts of pioglitazone HCl:excipients containing carboxylate groups and show disproportionation (open circles) vs. stressed 9:1 binary compacts of pioglitazone HCl:excipients with neutral or proton donating groups showing no disproportionation (open squares). Specificity for the HCl and Free base salt forms was found in the region from 7.0-11.0 2 theta and the XRPD spectra of the 5 day 40° C./75% RH samples are shown in FIG. 1. The XRPD confirmed that the binary compacts containing proton accepting carboxylate groups (SSF, NaCC, MgSt) accepted a proton from the pioglitazone HCl salt and caused the formation of pioglitazone free base. Binary compacts containing neutral or proton donating excipients (SA, SSt, X-PVP) were not able to accept a proton and consequently did not induce any significant disproportionation of pioglitazone HCl to the free base.

Subsequent studies probed the unique interaction of a 9:1 pioglitazone:MgSt binary compact. Compacts were stressed at multiple RH's ranging from 25%-75% RH and the NIR results are shown in Table 5. The RH observed between 31% RH and 35% RH correlates well with the known deliquescent point of 32% RH for the MgCl$_2$ salt. Therefore the interaction of MgSt with an acidic HCl salt forms in-situ MgCl$_2$ and would be applicable to any acidic HCl salt when combined with MgSt.

TABLE 5

9:1 Pioglitazone HCl:MgSt compacts stressed at 40° C. and various relative humidities indicating the formation of in-situ deliquescent MgCl$_2$ and producing a generic reaction that is applicable to any HCl salt + MgSt

| | | % of Initial PioHCl Remaining | | | | | |
|---|---|---|---|---|---|---|---|
| ID No. | Conditions | Day 0 | Day 0.5 | Day 1 | Day 6 | Day 14 | Day 16 |
| 90% PioHCl, 10% MgSt (4) | 40° C./ 25% RH | 100 | | | 97 | 96 | 96 |
| 90% PioHCl, 10% MgSt (4) | 40° C./ 31% RH | 100 | | | 94 | 95 | 96 |
| 90% PioHCl, 10% MgSt (4) | 40° C./ 35% RH | 100 | | | | | 73 |
| 90% PioHCl, 10% MgSt (4) | 40° C./ 75% RH | 100 | 68 | | | | |

The NIR and XRD both confirmed that conversion of the HCl salt to the free base form was most significant in the compacts containing MgSt. Therefore, pioglitazone HCl, MgSt and organic acid compacts were prepared to determine if organic acids could mitigate the observed disproportionation in the worst case excipient. The compacts were stressed at the worst case storage condition of 40° C./75% RH open dish and were quantitated using the previously described NIR model. The MR results in Table 6 demonstrate that MA and TA could inhibit disproportionation.

TABLE 6

Acidified Pioglitazone HCl:Excipient Compacts Stressed at 40° C. and 75% Relative Humidity

| | % of Initial PioHCl Remaining | | | | | |
|---|---|---|---|---|---|---|
| ID No. | Day 0 | Day 0.5 | Day 3 | Day 5 | Day 7 | Day 23 |
| 80% PioHCl, 10% MgSt, 10% MA (8) | 100 | 98 | 100 | 104 | 103 | 103 |
| 80% PioHCl, 10% MgSt, 10% FA (9) | 100 | | 75 | | | |
| 80% PioHCl, 10% MgSt, 10% TA (10) | 100 | | | 101 | | |

TABLE 6-continued

Acidified Pioglitazone HCl:Excipient Compacts
Stressed at 40° C. and 75% Relative Humidity

| | % of Initial PioHCl Remaining | | | | | |
|---|---|---|---|---|---|---|
| ID No. | Day 0 | Day 0.5 | Day 3 | Day 5 | Day 7 | Day 23 |
| 80% PioHCl, 10% MgSt, 10% CA (11) | 100 | 77 | 75 | 73 | | |
| 89% PioHCl, 9.5% MgSt, 1.5% MA (12) | 100 | | 73 | | 72 | |
| 87% PioHCl, 10% MgSt, 3% MA (13) | 100 | | 78 | | | |
| 85% PioHCl, 10% MgSt, 5% MA (14) | 100 | | 90 | | 93 | |
| 80% PioHCl, 10% MgSt, 10% OA (15) | 100 | | | 91 | | |

Figure 2:
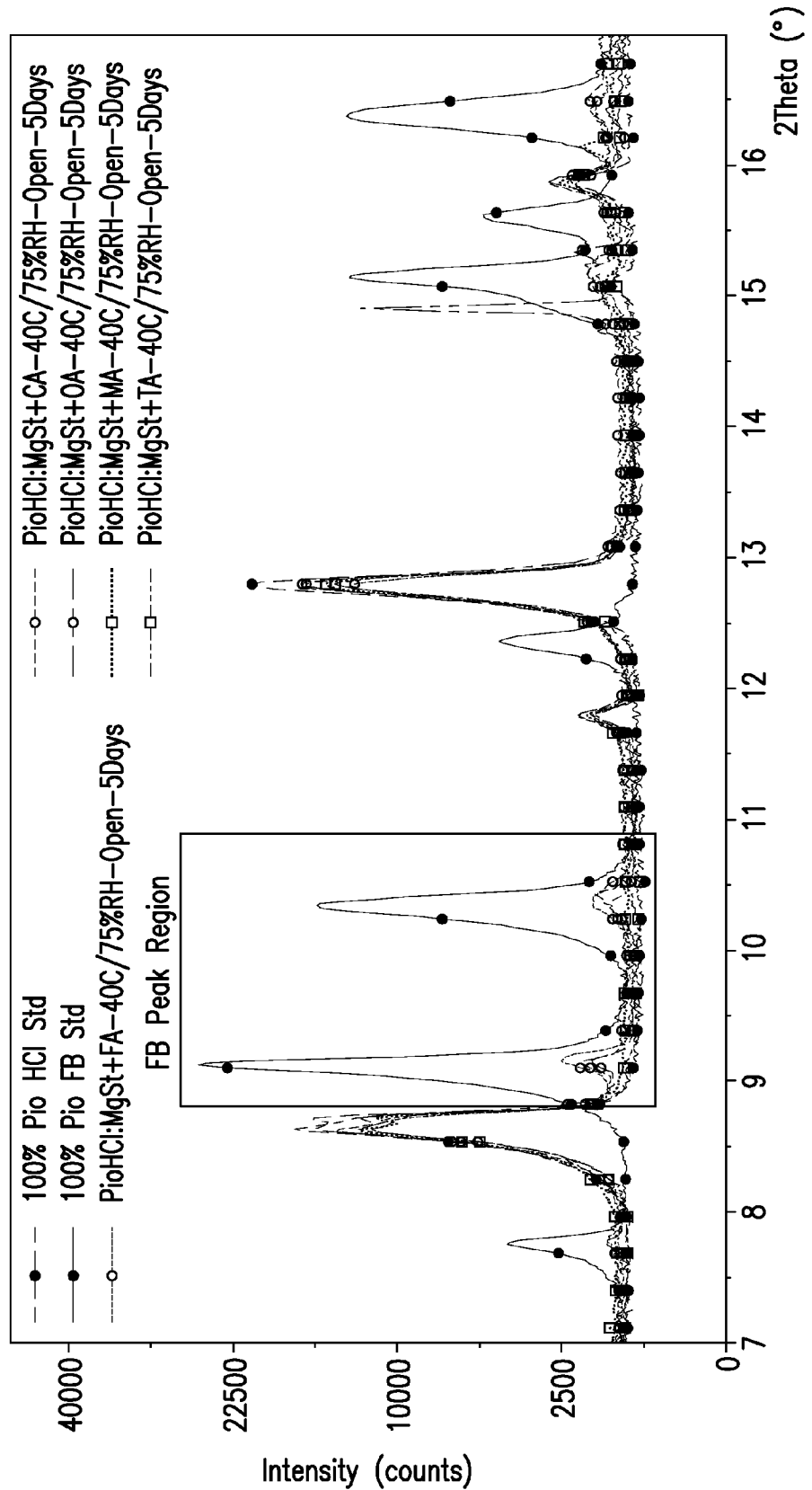
FIG. 2 shows X-ray powder diffraction of compacts of pioglitazone HCl and pioglitazone free base standards, and compacts of pioglitazone HCl with magnesium stearate and various organic acids.
Figure 3:
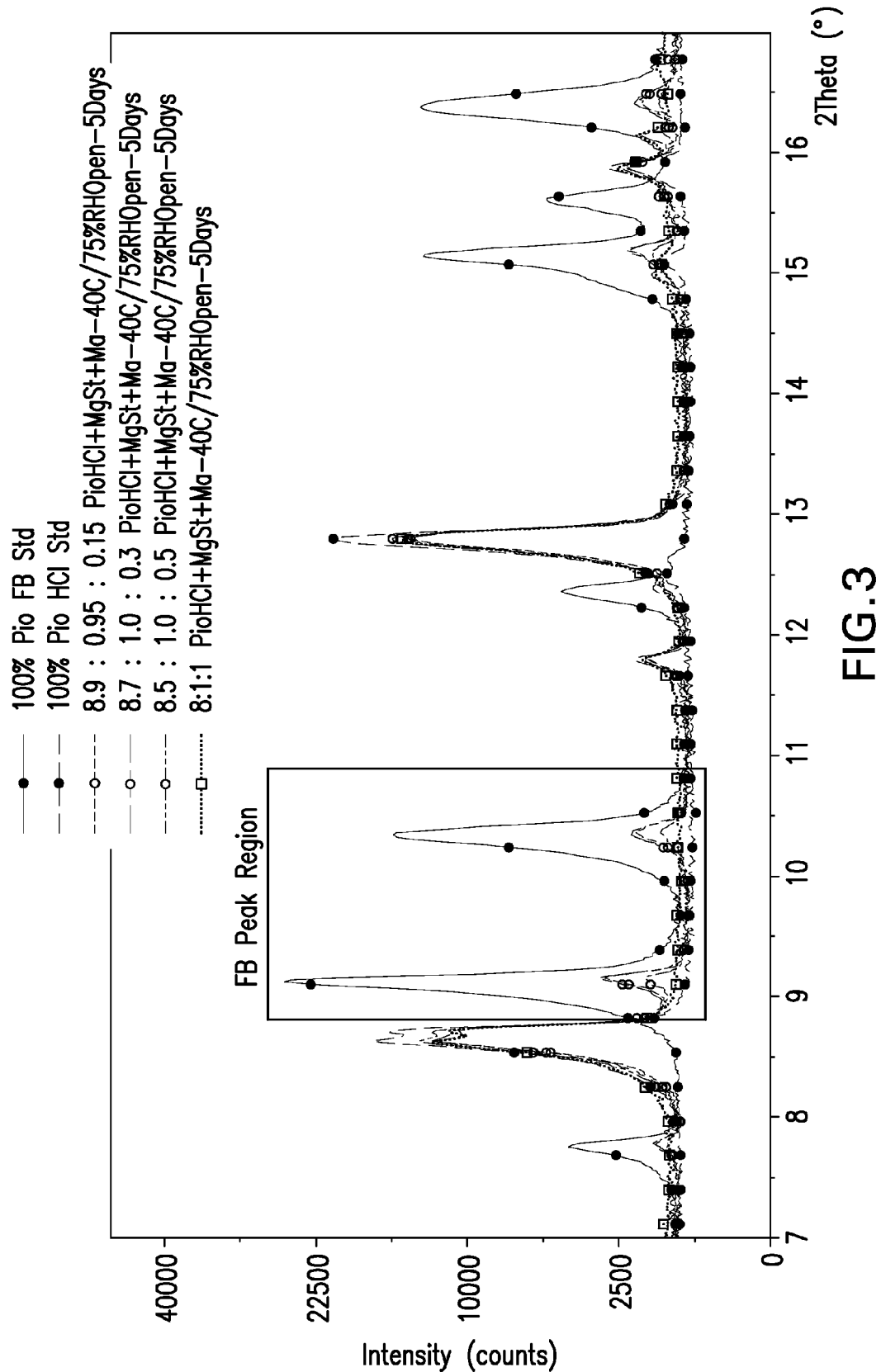
FIG. 3 shows X-ray powder diffraction of compacts of pioglitazone HCl and pioglitazone free base standards, and compacts of pioglitazone HCl with magnesium stearate and maleic acid at various ratios.

NIR results were confirmed using XRPD analysis of the binary compacts. FIG. 2 compares the XRPD spectra of the pioglitazone HCl and free base standards versus the various acidified compacts (samples 8-11). FIG. 2 shows X-ray powder diffraction of pioglitazone HCl and free base standards (solid circles), 40° C./75% RH open dish stressed pioglitazone HCl compacts containing MgSt with organic acids that successfully inhibit disproportionation (mA and TA, open squares) and organic acids that do not effectively inhibit disproportionation (FA, CA, and OA, open circles). The samples containing various levels of MA (samples 12-15) were also evaluated by XRPD in FIG. 3. FIG. 3 shows X-ray powder diffraction of pioglitazone HCl and free base standards (solid circles) vs. 40° C./75% RH open dish stressed pioglitazone HCl compacts containing MgSt with varying levels of MA (open symbols). A 1:1 ratio of MA to MgSt was required to inhibit disproportionation (open square) all other ratios (open circles) were not effective in inhibiting formation of free base.

The results in Table 6 and FIGS. 2 and 3 indicate that disproportionation was completely inhibited via acidification using either TA or MA in a 1:1 weight ratio with the carboxylate excipient species whereas FA, CA and OA were not effective in inhibiting disproportionation. Comparing the results for disproportionation inhibition with the organic acid properties in Table 1 strongly suggests that both the organic acid's pKa and solubility play a key role in preventing disproportionation. The organic acid inhibits disproportionation through the liberation of its acidic proton and the subsequent neutralization of the excipients' proton accepting carboxylate groups. This approach to inhibition of disproportionation via formulation acidification would be applicable to any acidic salt which is combined with excipients containing proton accepting carboxylate groups.

Acidification of Pioglitazone HCl Pseudo Formulation Compacts

The application of the acidified compacts was further investigated in a pseudo formulation matrix. Since the fillers may increase sample hygroscopicity, the binary mixtures were re-prepared and "diluted" using a filler matrix. The pseudo formulation NIR model was used to monitor the loss of HCl salt in the compacts listed in Table 2 (samples 16-28). The compacts were scanned at time zero and monitored throughout the studies.

The results in Table 7 for samples 16-21 demonstrate the deleterious effects that a basic carboxylate excipient would play on the disproportionation kinetics. In this study, the disproportionation reaction was rapid and had reached a plateau within 3 days. Similar to the binary compact studies, the pseudo formulation compacts containing MgSt exhibited the most significant loss of the HCl salt form.

TABLE 7

Pioglitazone HCl:Pseudo Formulation Excipient Compacts
Stressed at 40° C. and 75% Relative Humidity
% of Initial HCl Salt Form Remaining in Avicel:Mannitol Based
Formulations Stressed at 40° C./75% RH Open Dish

| | Time (Days) | | | | | | |
|---|---|---|---|---|---|---|---|
| ID No. | 0.16 | 3.0 | 3.5 | 4.0 | 5.0 | 7.0 | 10.0 |
| Pseudo Formulation 45% PioHCl, 50% 1:1 Avicel:Mannitol, 5% NaCC (16) | 99 | 87 | 88 | 87 | 87 | 88 | 86 |
| Pseudo Formulation 45% PioHCl, 50% 1:1 Avicel:Mannitol, 5% SST (17) | 102 | 103 | 102 | 103 | 101 | 105 | 104 |
| Pseudo Formulation 45% PioHCl, 50% 1:1 Avicel:Mannitol, 5% SSF (18) | 97 | 86 | 86 | 84 | 85 | 84 | 83 |
| Pseudo Formulation 45% PioHCl, 50% 1:1 Avicel:Mannitol, 5% X-PVP (19) | 100 | 100 | 100 | 98 | 102 | 103 | 101 |
| Pseudo Formulation 45% PioHCl, 50% 1:1 Avicel:Mannitol, 5% MgSt (20) | 80 | 69 | 69 | 69 | 68 | 68 | 67 |
| Pseudo Formulation 45% PioHCl, 50% 1:1 Avicel:Mannitol, 5% SA (21) | 104 | 102 | 103 | 101 | 103 | 104 | 102 |

| | Time (Days) | | | | | |
|---|---|---|---|---|---|---|
| ID No. | 12.0 | 14.0 | 17.0 | 19.0 | 24.0 | 28.0 |
| Pseudo Formulation 45% PioHCl, 50% 1:1 Avicel:Mannitol, 5% NaCC (16) | 85 | 86 | 85 | 85 | 84 | 84 |
| Pseudo Formulation 45% PioHCl, 50% 1:1 Avicel:Mannitol, 5% SST (17) | 104 | 104 | 104 | 103 | 103 | 103 |
| Pseudo Formulation 45% PioHCl, 50% 1:1 Avicel:Mannitol, 5% SSF (18) | 82 | 83 | 83 | 83 | 83 | 83 |
| Pseudo Formulation 45% PioHCl, 50% 1:1 Avicel:Mannitol, 5% X-PVP (19) | 100 | 101 | 100 | 101 | 101 | 100 |
| Pseudo Formulation 45% PioHCl, 50% 1:1 Avicel:Mannitol, 5% MgSt (20) | 67 | 66 | 66 | 66 | 65 | 65 |
| Pseudo Formulation 45% PioHCl, 50% 1:1 Avicel:Mannitol, 5% SA (21) | 101 | 102 | 102 | 100 | 100 | 99 |

Figure 4:
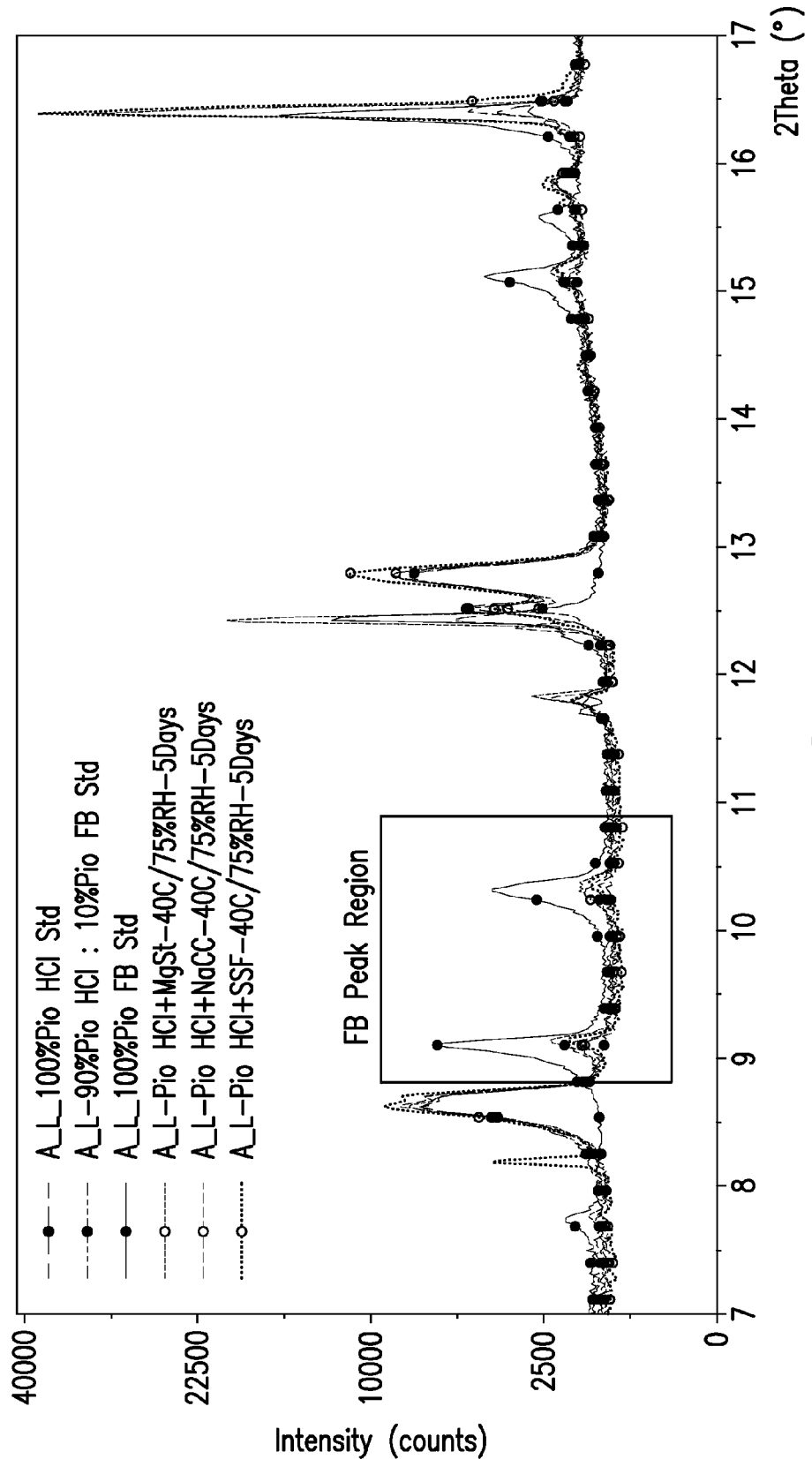
FIG. 4 shows X-ray powder diffraction of pseudo formulations of pioglitazone HCl and various excipients.

Previous acidification data from Table 6 suggests that the disproportionation reaction could be inhibited through acidification with either TA or MA. FIG. 4 shows X-ray powder diffraction of pseudo formulations of pioglitazone HCl and free base standards (solid circles) vs. pseudo formulations containing pioglitazone HCl and carboxylate excipients stressed at 40° C./75% RH in an open dish and showed conversion to the free base form of pioglitazone. The XRPD results in FIG. 4 indicate that basic carboxylate excipients induce disproportionation in pseudo formations within 5 days of storage at 40° C./75% RH conditions. Table 7 results also show that the MgSt containing compacts were the most likely compact to induce disproportionation. Based on these results, samples 22-28 were prepared, stressed and analyzed to determine if adding an organic acid could inhibit disproportionation within a pseudo formulation containing proton accepting excipients.

Figure 5:
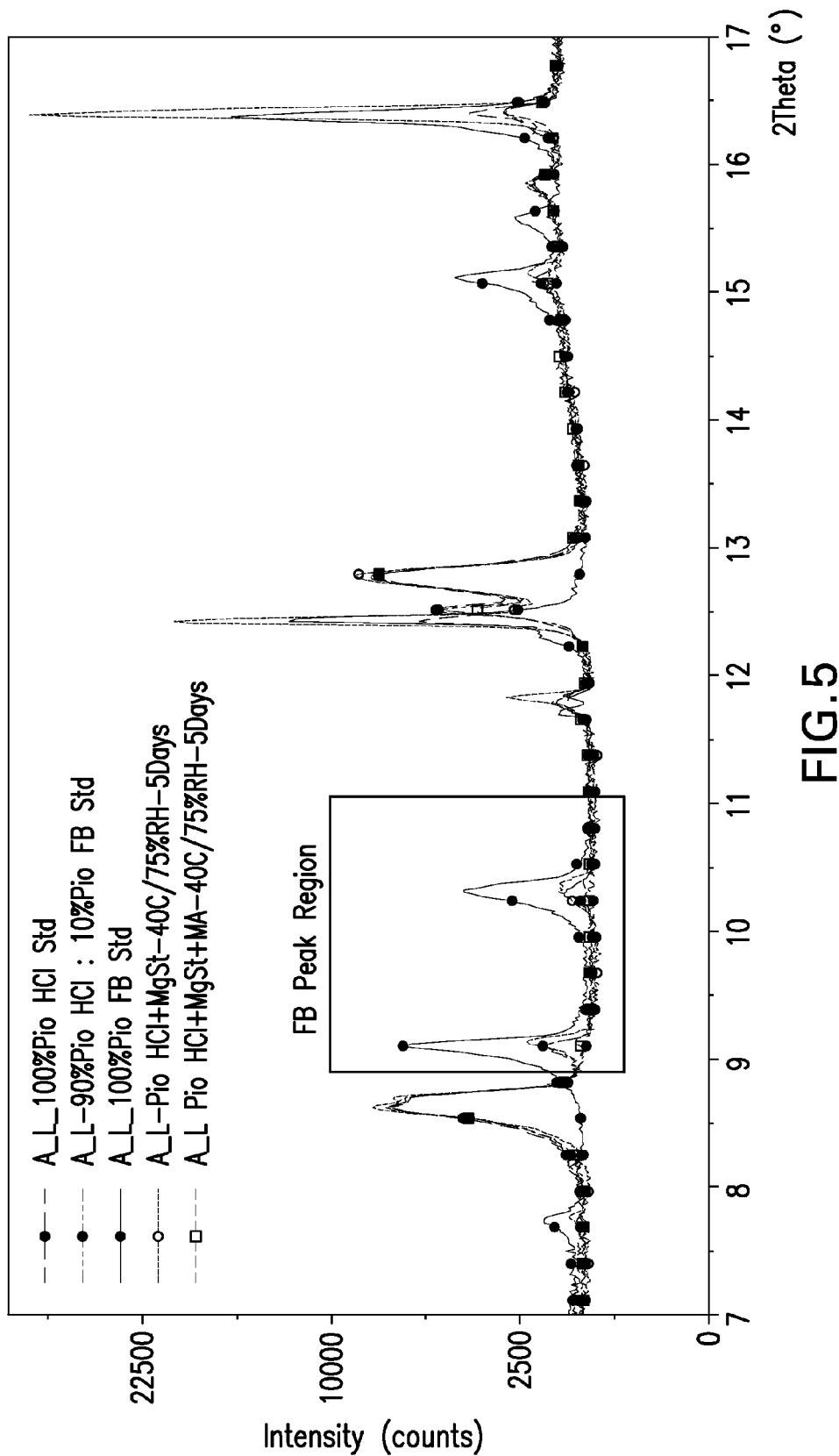
FIG. 5 shows X-ray powder diffraction of pseudo formulations of pioglitazone HCl and magnesium stearate, with and without maleic acid.
Figure 6:
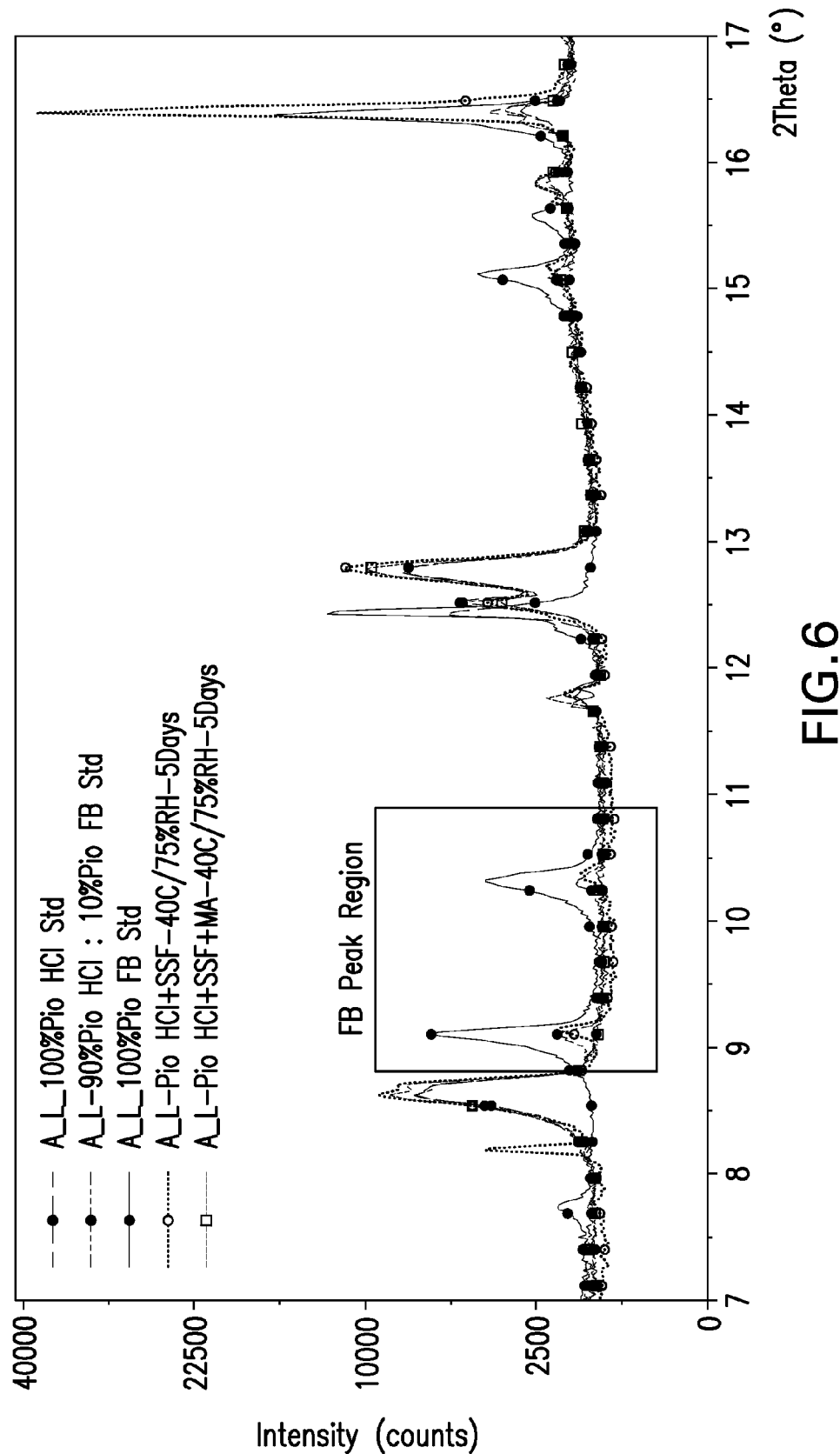
FIG. 6 shows X-ray powder diffraction of pseudo formulations of pioglitazone HCl and sodium stearyl fumarate, with and without maleic acid.
Figure 7:
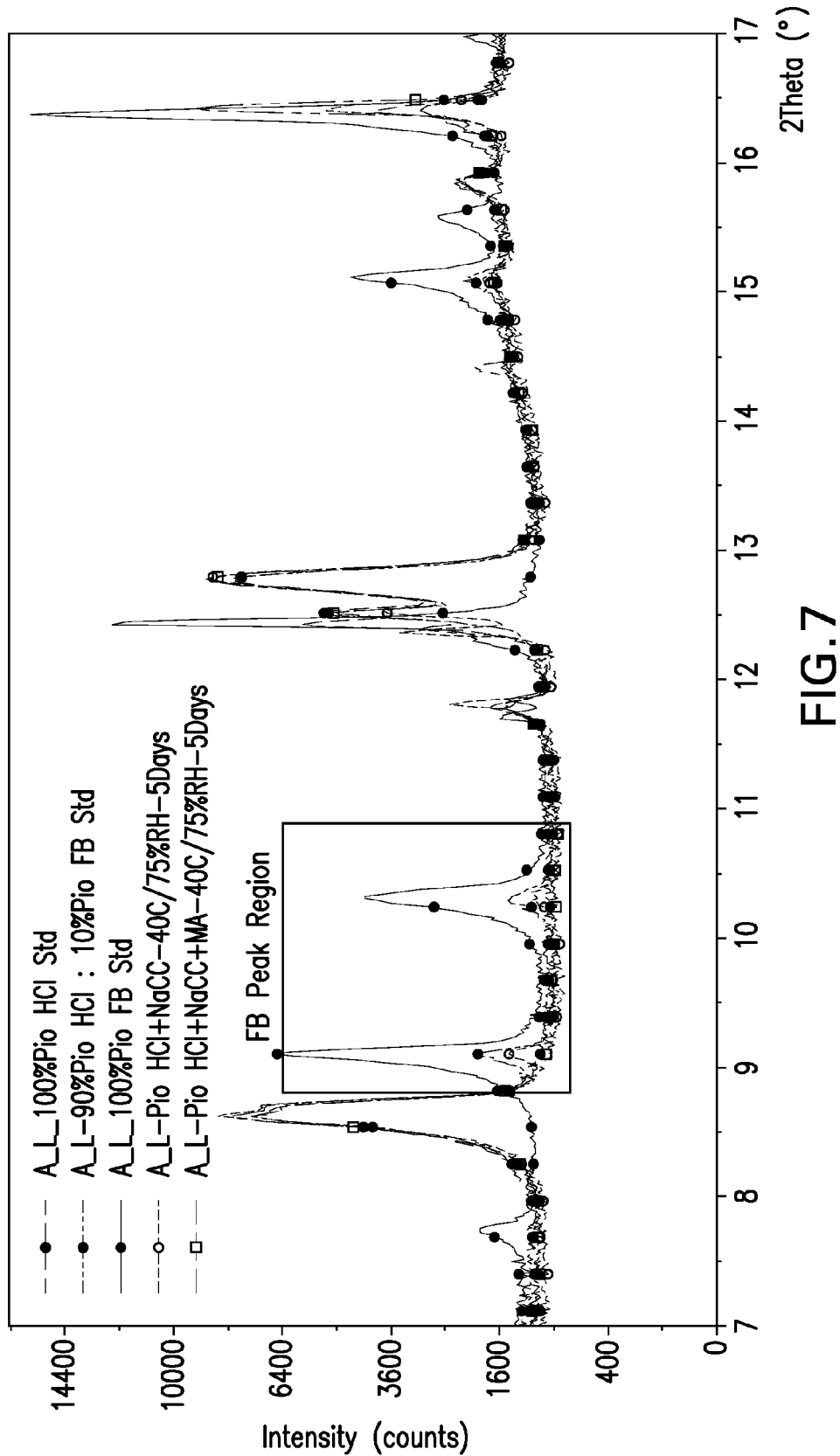
FIG. 7 shows X-ray powder diffraction of pseudo formulations of pioglitazone HCl and sodium croscarmellose, with and without maleic acid.

Additional X-ray diffraction studies were shown in FIGS. 5-7. FIG. 5 shows X-ray powder diffraction comparing pseudo formulations of pioglitazone HCl and free base standards (solid circles), stressed (40° C./75% RH in open dish) pseudo formulations containing pseudo formulations containing pioglitazone HCl and MgSt (open circles) and pseudo formulations containing pioglitazone HCl, MgSt, MA (open squares). The inhibition of free base formation was achieved with MA showing inhibition of free base conversion by MA. FIG. 6 shows X-ray powder diffraction of pseudo formulations of pioglitazone HCl and free base standards (solid circles) vs. pseudo formulations containing pioglitazone HCl, SSF, and MA (open squares) stressed at 40° C./75% RH open dish showing inhibition of free base conversion by MA. FIG. 7 shows X-ray powder diffraction of pseudo formulations of pioglitazone HCl and free base standards (solid circles) vs. pseudo formulations containing pioglitazone HCl, NaCC, and MA (open squares) stressed at 40° C./75% RH open dish showing inhibition of free base conversion by MA.

In summary, the XRPD results of the compacts stressed at 40° C./75% RH open dish in FIGS. 4-7 demonstrate that disproportionation was inhibited by the inclusion of an organic acid with high solubility and a low pKa.

TABLE 8

Pioglitazone HCl:Acidified Pseudo Formulation Excipient Compacts Stressed at 40° C. and 75% Relative Humidity

| | % of Initial PioHCl Remaining | | | |
|---|---|---|---|---|
| ID No. | Day 0 | Day 1 | Day 2 | Day 5 |
| Pseudo Formulation 50% PioHCl, 45% 1:1 Avicel:Lactose, 5% NaCC (22) | 100 | 99 | 96 | 95 |
| Pseudo Formulation 43% PioHCl, 47% 1:1 Avicel:Lactose, 5% NaCC, 5% MA (23) | 100 | 97 | 95 | |
| Pseudo Formulation 50% PioHCl, 45% 1:1 Avicel:Lactose, 5% SSF (24) | 100 | 96 | 94 | 94 |
| Pseudo Formulation 43% PioHCl, 47% 1:1 Avicel:Lactose, 5% SSF, 5% MA (25) | 100 | 101 | 101 | |
| Pseudo Formulation 50% PioHCl, 45% 1:1 Avicel:Lactose, 5% MgSt (26) | 100 | 83 | 82 | 82 |
| Pseudo Formulation 43% PioHCl, 47% 1:1 Avicel:Lactose, 5% MgSt, 5% MA (27) | 100 | 98 | 98 | |
| Pseudo Formulation 43% PioHCl, 47% 1:1 Avicel:Lactose, 5% MgSt, 5% FA (28) | 100 | | | 85 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pharmaceutical formulation comprising:
   (1) a pharmaceutically acceptable acid salt of an active pharmaceutical ingredient, and
   (2) a solid pharmaceutically acceptable organic acid in a sufficient amount to reduce disproportionation, wherein the ratio of the pharmaceutically acceptable organic acid to excipient that promotes disproportionation is from about 1:6 to about 1:1, respectively,
   wherein the pharmaceutically acceptable acid salt of the active pharmaceutical ingredient has a pKa of less than about 6.0, and
   wherein the solid pharmaceutically acceptable organic acid has a pKa of less than about 4.0 and an aqueous solubility in the range of about 500 to about 2000 milligrams per milliliter.

2. The pharmaceutical formulation of claim 1, wherein the solid pharmaceutically acceptable organic acid is maleic acid or tartaric acid.

3. The pharmaceutical formulation of claim 1, further comprising an excipient that promotes disproportionation.

4. The pharmaceutical formulation of claim 3, wherein the excipient that promotes disproportionation contains carboxylate salt functional groups.

5. The pharmaceutical formulation of claim 4, wherein the excipient that promotes disproportionation is magnesium stearate, sodium stearyl fumarate, or croscarmellose sodium, or combinations thereof.

6. The pharmaceutical formulation of claim 5, wherein the excipient that promotes disproportionation is magnesium stearate.

7. The pharmaceutical formulation of claim 1, wherein the ratio of the pharmaceutically acceptable organic acid to excipient that promotes disproportionation is about 1:1, respectively.

8. A pharmaceutical formulation comprising:
   (1) a pharmaceutical acceptable acid salt of pioglitazone,
   (2) a solid pharmaceutically acceptable organic acid selected from the group consisting of maleic acid or tartaric acid, and
   (3) an excipient that promotes disproportionation,
   wherein the ratio by weight of the solid pharmaceutically acceptable organic acid to excipient is from about 1:6 to about 1:1.

9. The pharmaceutical formulation of claim 8, wherein the ratio by weight of the solid pharmaceutically acceptable organic acid to excipient that promotes disproportionation is 1:1.

10. The pharmaceutical formulation of claim 1, wherein the excipient that promotes disproportionation is selected from the group consisting of magnesium stearate, sodium stearyl fumarate, croscarmellose sodium, or combinations thereof.

11. A method of manufacturing a pharmaceutical formulation comprising an active pharmaceutical ingredient and an excipient promoting disproportionation, comprising the step of adding a pharmaceutically acceptable organic acid in a sufficient amount to reduce disproportionation, wherein the pharmaceutically acceptable organic acid is added in a sufficient amount such that the ratio of the pharmaceutically acceptable organic acid to excipient that promotes disproportionation is from about 1:6 to about 1:1, wherein the solid pharmaceutically acceptable organic acid has a pKa of less than about 4.0 and an aqueous solubility in the range of about 500 to about 2000 milligrams per milliliter.

12. The method of claim 11, wherein the pharmaceutically acceptable organic acid is added in a sufficient amount such that the ratio of the pharmaceutically acceptable organic acid to excipient that promotes disproportionation is about 1:1.

* * * * *